United States Patent [19]

Cook, III

[11] Patent Number: 4,893,323

[45] Date of Patent: Jan. 9, 1990

[54] COMBINATION PORTABLE X-RAY TABLE AND STRETCHER

[76] Inventor: Charles F. Cook, III, 1437 Dunigan Pl., Manteca, Calif. 95336

[21] Appl. No.: 221,437

[22] Filed: Jul. 19, 1988

[51] Int. Cl.⁴ .............................................. A61B 6/04
[52] U.S. Cl. .................... 378/208; 378/177; 269/328
[58] Field of Search ............... 378/208, 209, 177, 180, 378/167; 269/328

[56] References Cited

U.S. PATENT DOCUMENTS

| | | | |
|---|---|---|---|
| 2,504,697 | 9/1946 | Kearsley | 378/177 |
| 3,065,344 | 10/1959 | Cheruenka | 378/177 |
| 3,648,305 | 3/1972 | Ersek | 378/180 |
| 4,156,145 | 5/1979 | Weatherholt | 378/208 |
| 4,779,858 | 10/1988 | Saussereau | 269/328 |

FOREIGN PATENT DOCUMENTS 2432525 2/1975 Fed. Rep. of Germany ...... 378/208

Primary Examiner—Carolyn E. Fields
Assistant Examiner—Joseph A. Hynds
Attorney, Agent, or Firm—Henry P. Sartorio

[57] ABSTRACT

A combination portable x-ray table and stretcher immobilizes an emergency patient from time of pick-up through x-ray examination without further movement or manipulation of the patient relative to the table/stretcher, thus reducing the risk of further injury. The table/stretcher has a flat rigid low x-ray attenuation (1 mm aluminum equivalent or less) top support on which the patient is placed. The top is spaced apart from a base by a pair of side supports. The device also has an open interior space or channel accessed from openings at each end in which x-ray film cassettes can be positioned under the patient without touching the patient. Transparent side supports allow visual observation of film placement for accurate positioning.

16 Claims, 1 Drawing Sheet

COMBINATION PORTABLE X-RAY TABLE AND STRETCHER

BACKGROUND OF THE INVENTION

The invention relates generally to medical apparatus and more particularly to apparatus for transporting a patient in conjunction with performing x-ray examination while the patient is on the apparatus.

A person who has been seriously injured in an accident or from a sudden illness usually will be transported by emergency personnel to a hospital or other site where medical treatment can be rendered. A first step in determining the nature and extent of the injury is to take x-rays of the patient before appropriate treatment can be given. Therefore, it is extremely important that the transportation of the patient and x-ray procedure be performed in a manner which minimizes any further risk of injury to the patient. Thus, it is desirable to essentially immobilize the patient from the time the patient is first placed on the transport device until after the x-rays are taken so that the injury will not be aggravated. Unfortunately, present techniques generally result in undesirable manipulation of the patient, such as positioning, lifting, bending, etc. during x-ray procedures and examinations. This patient movement may be detrimental to the patient, in the worst case even life threatening; the movement may also require the suspension of other procedures (e.g. CPR) or result in repeated examinations or procedures which cause untimely delays when time may be a critical factor. No patient movement is warranted when a head-neck-spine injury is suspected or after the placement of an endotracheal tube for life support and breathing. Lifting the head to place an x-ray film under the neck to take a cervical-spine examination could result in paralysis or death of a patient. Reducing patient movement also will relieve and possibly reduce injuries to the personnel who are handling the patient.

The most commonly used transport device in the field is a simple flat board; however, other more complicated stretchers can also be used. A rigid surface is desirable because it allows CPR to be performed. Although these devices are fine for transporting the patient, they create a problem when it is necessary to x-ray the patient since some movement of the patient will be necessary, either to transfer the patient entirely to an x-ray table or to place a film under the patient while still on the transport device. These transport devices are made of materials which contain artifacts or internal imperfections so that x-rays taken through the device may be inaccurate; therefore the patient should not be x-rayed through the device.

Therefore it is desirable to have a transport device which permits x-ray examination of the patient without any movement of the patient relative to the transport device and without interfering with the x-ray quality. However, presently available devices do not provide this combination of characteristics with its attendant decrease in patient risk and increase in patient safety.

U.S. Pat. No. 4,067,079 to Buchman shows a patient shifting aid comprising a flexible plastic slab.

U.S. Pat. No. 4,156,145 to Weatherholt shows an x-ray support device having a base surface for resting on a flat surface and a movable upper surface for receiving the patient torso, with aperture means in the device for placing x-ray film.

U.S. Pat. No. 3,358,141 to Hoffmann shows a board with immobilizer straps for x-raying infants. U.S. Pat. No. 3,264,659 to Magni shows a litter comprising a first frame which fits within a second frame. U.S. Pat. No. 3,304,116 to Stryker shows a wheeled carriage which can support a stretcher. U.S. Pat. No. 4,012,799 to Rutherford shows a sled board for transferring a patient from one bed to another. U.S. Pat. No. 3,329,978 to Porter shows a stretcher-operating table bridging panel. U.S. Pat. No. 2,528,048 to Gilleland shows a wheeled stretcher with means to transfer a patient to another support. U.S. Pat. No. 3,373,454 to Curtis shows a segmented stretcher with individually movable sections. U.S. Pat. No. 3,962,736 to Fedele shows a device for moving a patient in bed which has a base and support platform which slides on the base. U.S. Pat. No. 4,145,612 to Cooper shows a multilayer composite x-ray support stretcher. U.S. Pat. No. 3,737,923 to Prolo shows a cervical spine immobilization device.

None of the prior art references show a medical device which provides sufficient immobilization of the patient from initial transport through an x-ray examination to minimize risk or additional injury to the patient.

State of the art x-ray tables found in modern hospitals are made of rigid, high strength, uniform, low attenuation (1 mm aluminum equivalent or less) materials which permit effective x-ray examination while protecting the patient. X-ray films are placed in table drawers under the patient without moving the patient. The table material has been approved for this use because of its uniform high transparency or transmission (low attenuation or absorption) to x-rays (radiolucence) which produces no interference on the x-ray film. Unfortunately, these tables are not portable and a patient must be transferred thereto from a transport device for examination.

SUMMARY OF THE INVENTION

Accordingly, it is an object of the invention to provide a medical device which can be used to both transport a patient and perform x-ray examination without unnecessary movement of the patient.

It is also an object of the invention to provide a medical device which immobilizes a patient during transport and subsequent x-ray examination without transfer from the device.

It is another object of the invention to provide a medical device which eliminates undesirable manipulation of a patient during x-ray and other medical examination.

It is a further object of the invention to provide a medical device which performs the dual functions of a stretcher and x-ray table.

The invention is a combination portable x-ray table and stretcher which has a rigid flat upper support which maintains a patient's position and/or configuration from the time a person having an injury or illness is first attended and transported through a complete and thorough medical and x-ray examination without further patient manipulation. The device is placed directly under an injured or ill person at the scene of an accident or injury to immobilize the person for transport to a facility where medical assistance is available. Thus the only necessary movement of a patient is the initial placement of the person onto the transport device; the present invention insures that this movement of the patient is the last movement of the patient required until after an x-ray examination of the patient has been performed. The rigid flat upper support is mounted in a spaced relationship to a base by means of side supports which are preferably transparent. The space between the upper support and base is open at the ends of the device so that x-ray film may be placed in various positions beneath the patient's body; the transparent side supports allow for exact placement. The upper support is made of the same rigid, high strength, low attenuation (1 mm Al equivalent or less) material as a hospital x-ray table to permit x-rays of the patient to be taken through the upper support with no interference. Additional features of the invention include a plurality of slots spaced along the sides for gripping and lifting the device, and a plurality of spaced runners connected below the base from side to side to give additional strength to the base and raise the device for easier gripping and lifting.

DETAILED DESCRIPTION OF THE PREFERRED EMBODIMENT

Figure 1:
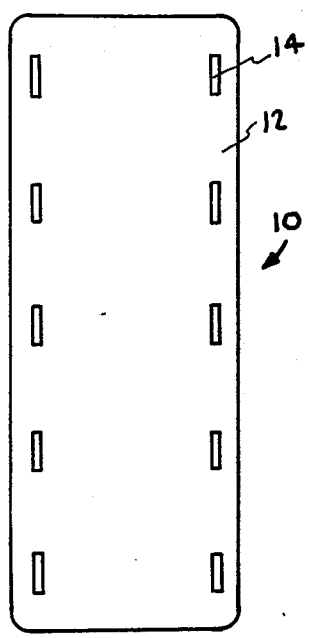
FIG. 1 is a top view of a combination portable x-ray table and stretcher showing hand holes for gripping and lifting and for patient immobilization devices.

As shown in FIG. 1, a combination portable x-ray table and stretcher device 10, in accordance with the invention, has a substantially rectangular rigid flat top support 12 with a plurality of hand holes or slots 14 extending therethrough spaced along and near the two sides of support 12. Top support 12 is made of the same type of material as nonportable hospital x-ray tables so that it is highly x-ray transparent and without artifacts. The top support 12 provides support for a patient while permitting x-rays of the patient to be taken therethrough. Near the two sides of top support 12 are slots 14 for gripping and lifting device 10; in addition slots 12 can be used for devices that immobilize and support the patient, e.g., attachment of straps to hold the patient.

Figure 2:
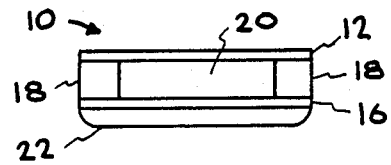
FIG. 2 is an end view showing top, sides and base defining a central channel for x-ray film cassette placement.

As shown in FIG. 2, top support 12 of device 10 is mounted in a spaced relationship over a rigid base 16 by means of rigid side supports 18, defining an open space or channel 20 therebetween. Top support 12 rests on and is fastened to two side supports 18 which are mounted on base 16. Top support 12, side supports 16 and base 18 enclose an open space or channel 20 which runs down the entire length of device 10 between the two open ends. This channel 20 allows an x-ray film cassette to be placed directly under the area of interest without moving the patient. Side supports 18 are preferably transparent to permit visual positioning of the x-ray film for proper placement. Each side support 18 can be formed of a single vertical strip, or a spaced parallel pair of such vertical strips for greater rigidity and support. The base 16 provides support for cassette positioning. Connected below base 16 are a plurality of spaced parallel runners 22 which run from side to side (i.e. are parallel to the ends) to give additional strength to base 16 and to raise device 10 off the ground or other surface for easier gripping and lifting (using slots 14). The end of runners 22 are rounded for rolling device 10 if necessary.

Figure 3:
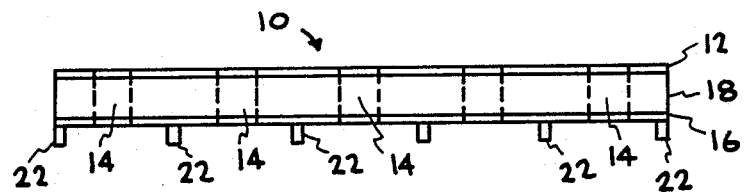
FIG. 3 is a side view showing top, sides and base with runners.

As shown in FIG. 3, top support 12 is mounted to base 16 by side support 18. Hand holes or slots 14 extend through device 10. Runners 22 are placed on the bottom of base 16 to provide space for grabbing slots 14.

Figure 4:
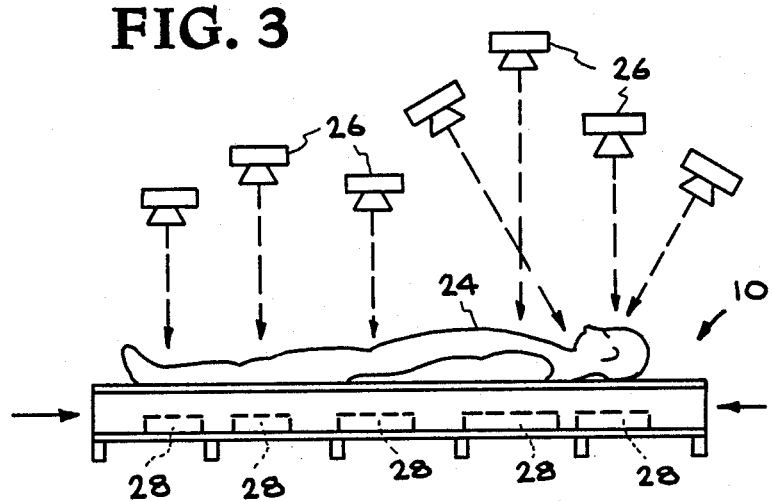
FIG. 4 is a side view showing a patient being medically examined by x-rays from a variety of positions and angles.

As shown in FIG. 4, a patient 24 placed on device 10 is examined by means of a movable or portable x-ray unit 26 without any manipulation or movement of the patient. X-ray film cassettes 28 are placed in the channel 20 of device 10 from either end and are visible through transparent side support 18. The cassettes 28 sit on base 16. X-rays can be taken of the patient 24 at a number of different positions and angles, e.g., head, neck, chest, etc., as illustrated by the multiple positions of x-ray unit 26 and film cassettes 28; therefore, any desired x-ray should be obtainable without the need to move the patient. The patient, of course, can be in any position, e.g., prone, supine, or on the side, in which the patient was placed on device 10 prior to transport.

Figure 5:
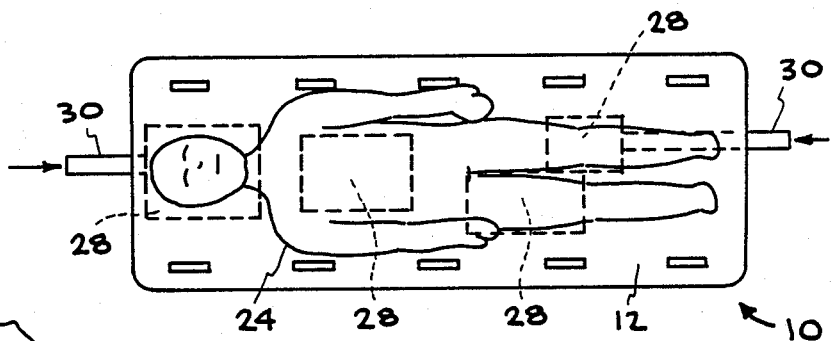
FIG. 5 is a top view illustrating various placements of x-ray film relative to a patient.

As shown in FIG. 5, a patient 24 is lying on top support 12 of device 10. Medical x-ray film cassettes 28 of different sizes may be properly positioned beneath the patient in channel 20 of device 10 for various medical exams, e.g., head, neck, chest, lower abdomen, etc. The cassettes 28 are positioned by means of a push-stick 30 from either open end of the device 10. The cassettes 28 are positioned in the interior space or channel 20 of the device 10 in the correct position under the patient 24. After x-ray exposure, cassette 28 is removed by retracting push-stick 30.

Figure 6:
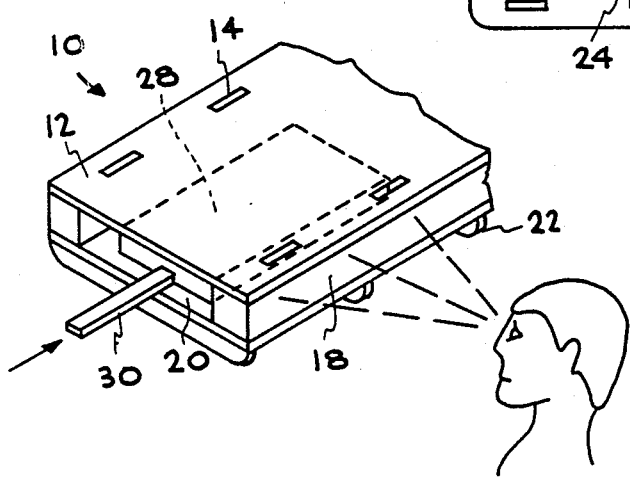
FIG. 6 is a perspective view which shows an x-ray film cassette being placed, looking through a transparent side for positioning.

As shown in FIG. 6, an x-ray technician 32 visually positions a cassette 30 in channel 20 of device 10 by viewing the position through a transparent side support 18 and moving the push-stick 30 until the cassette 28 is in the desired position under the patient (not shown) lying on the top support 12.

In an exemplary embodiment of the invention, the combination portable x-ray table and stretcher device is 20 inches wide (or less, to accommodate its placement on an emergency gurney), 72 inches long (entire body length) and 1-11/16 inches high. The top support is 0.25 inches thick and made of a fiber-resin material. Near the sides of the device are slots 3½ inches long by 1 inch wide for gripping and lifting. Each side support is approximately 2¼ inches wide by 72 inches long by ⅞ inch high. The base is 1/16 inch thick and the runners are ½ inch high, ½ inch wide and 20 inches long. The sides are made of acrylic plastic (Plexiglass) and the base of aluminum (perforated). The top support could also be made of a phenolic material or other materials which would be approved for nonportable hospital x-ray tables. The top support material should have a low x-ray attenuation (about 1 mm aluminum equivalent or less). A strong light weight material is preferred so that the total weight of the device is minimized.

The invention can be used from the time of patient pick-up through complete x-ray examination and even beyond to further medical/surgical procedures. Once a patient is placed on the device, the patient should not have to be moved/manipulated in any way relative to the device during transport to a medical facility and subsequent x-ray examination by means of portable x-ray equipment. Thereby, the possibility of aggravating or compounding patient injuries is significantly reduced. The device increases the number and type of examinations that can be performed, with less employee/patient contact. Emergency technicians are often highly skilled, but in responding to an accident or sudden illness must focus on a primary objective—providing life support treatment such as CPR and transporting the patient to a hospital for full evaluation and treatment. By using the device of the invention CPR can be provided almost without interruption while x-ray film is being placed and retrieved. Once an endotracheal tube has been positioned in the trachea-lung area, the possibility of moving the tube during x-ray examination is eliminated. Patients with neck and spinal injuries can be more completely immobilized to reduce further injury. Movement of the patient by emergency personnel could result in further injuries to the patient and also in injuries to the emergency personnel. Thus, the invention reduces or eliminates patient manipulation until proper medical treatment can be given for the type of injury involved, while increasing the number and type of examinations that can be performed (which might otherwise be postponed until the patient is moved) and decreases the need to repeat examinations because they could not be performed right the first time. The invention could also be used for other purposes, such as examination of a body in a coroner's case. In this situation, the invention reduces the amount of manipulation of the body required, thereby reducing risk of injury to the employee.

Changes and modifications in the specifically described embodiments can be carried out without departing from the scope of the invention which is intended to be limited only by the scope of the appended claims.

I claim:

1. A portable apparatus for immobilizing a patient during transportation and subsequent x-ray examination, comprising:
   a substantially rectangular base;
   a pair of transparent side supports mounted to the base and extending along two opposed sides thereof;
   a flat, rigid, low x-ray attenuation top support mounted to the side supports in a spaced relation to the base, and defining with the base and side supports an open channel comprising means for receiving of an x-ray cassette and extending between two open ends of the apparatus;
   the base, side supports and top support forming a portable unit.

2. Apparatus of claim 1 wherein the top support is made of a fiber-resin material or a phenolic material.

3. Apparatus of claim 1 further comprising a plurality of spaced runners mounted below the base and extending between the two sides.

4. Apparatus of claim 3 wherein the runners have rounded ends.

5. Apparatus of claim 1 further comprising a plurality of vertical slots formed therethrough along and near the two sides for gripping and lifting the apparatus and for securing patient immobilization means.

6. Apparatus of claim 1 wherein the base and top support are about 72 inches long and about 20 inches wide, and the side supports are about $\frac{7}{8}$ inch high.

7. Apparatus of claim 1 wherein the side supports are formed of acrylic plastic.

8. Apparatus of claim 6 wherein the side supports are each about 2$\frac{1}{2}$ inches wide.

9. Apparatus of claim 8 wherein each side support is formed of a pair of spaced parallel strips.

10. A portable apparatus for immobilizing a patient during transportation and subsequent x-ray examination, comprising:
    a substantially rectangular base;
    a pair of transparent side supports mounted to the base and extending along two opposed sides thereof;
    a flat, rigid, low x-ray attenuation top support made of a material with an aluminum equivalence of about 1 mm or less and mounted to the side supports in a spaced relation to the base, and defining with the base and side supports an open channel comprising means for the insertion of an x-ray cassette and extending between two open ends of the apparatus;
    the base, side supports and top support forming a portable unit.

11. Apparatus of claim 10 further comprising a plurality of spaced runners mounted below the base and extending between the two sides.

12. Apparatus of claim 11 wherein the runners have rounded ends.

13. Apparatus of claim 10 further comprising a plurality of vertical slots formed therethrough along and near the two sides for gripping and lifting the apparatus and for securing patient immobilization means.

14. Apparatus of claim 10 wherein the base and top support are about 72 inches long and about 20 inches wide, and the side supports are about $\frac{7}{8}$ inch high.

15. Apparatus of claim 10 wherein the side supports are formed of acrylic plastic.

16. Apparatus of claim 10 wherein each side support is formed of a pair of spaced parallel strips.

* * * * *